United States Patent [19]

Kolar

[11] Patent Number: 4,686,193
[45] Date of Patent: Aug. 11, 1987

[54] BETA-D-GALACTOSE DERIVATIVES AND THEIR USE

[75] Inventor: Cenek Kolar, Marburg, Fed. Rep. of Germany

[73] Assignee: Behringwerke Aktiengesellschaft, Marburg, Fed. Rep. of Germany

[21] Appl. No.: 498,732

[22] Filed: May 27, 1983

[30] Foreign Application Priority Data

May 29, 1982 [DE] Fed. Rep. of Germany ....... 3220427

[51] Int. Cl.$^4$ .................... G01N 33/536; C07H 15/04
[52] U.S. Cl. ..................................... 436/536; 436/518; 536/17.9; 536/4.1; 536/53; 536/55; 514/25
[58] Field of Search .......................... 536/4.1, 17.9, 53; 436/536, 518; 424/180; 514/25

[56] References Cited

U.S. PATENT DOCUMENTS 4,137,401  1/1979  Lemieux et al. .................... 536/4.1
4,228,274  10/1980 Ponpipom et al. ................. 536/17.9
4,442,284  4/1984  Kolar et al. ........................ 536/4.1

OTHER PUBLICATIONS

Tetrahedron Letters, vol. 22, No. 15 (1981), pp. 1387–1390.
Carbohydrate Research, vol. 101, No. 2, Mar. 1982, pp. 271–277.

Primary Examiner—Johnnie R. Brown
Assistant Examiner—Elli Peselel
Attorney, Agent, or Firm—Finnegan, Henderson Farabow, Garrett & Dunner

[57] ABSTRACT

New compounds of the general formula I

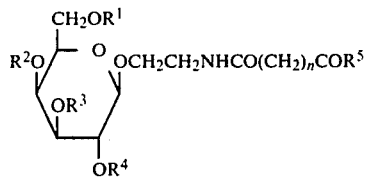

in which
R$^1$ and R$^2$ each denote a hydrogen atom or an acyl or benzyl protective group,
R$^1$ and R$^2$ together denote an alkylidene or benzylidene protective group,
R$^4$ denotes a hydrogen atom, an acyl or benzyl protective group or a 2,3,4-tri-O-benzyl-α-L-fucopyranosyl or α-L-fucopyranosyl radical,
R$^5$ denotes H, OH, NH$_2$, NHNH$_2$, N$_3$, O-alkyl, O-aryl, NH—(CH$_2$)$_m$NH$_2$, where m=2–5, lysine, polylysine or a carrier,
n denotes a number from 1 to 10 and
R$^3$ denotes a hydrogen atom, an acyl or benzyl protective group or an α-D-glycopyranosyl radical of the general formula II

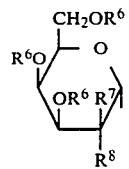

in which
R$^6$ denotes a hydrogen atom or an acyl or benzyl protective group,
R$^7$ denotes a hydrogen atom or halogen and
R$^8$ denotes a hydrogen atom, an acyloxy or benzyloxy group or an azido, amino, acetamido or hydroxyl group, a process for their preparation and their use, when bonded to a carrier, as synthetic antigens, glycolipids or immuno-adsorbents, are described.

6 Claims, No Drawings

BETA-D-GALACTOSE DERIVATIVES AND THEIR USE

The invention relates to new compounds of the general formula I

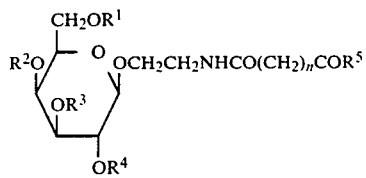

in which
R$^1$ and R$^2$ each denote a hydrogen atom or an acyl or benzyl protective group,
R$^1$ and R$^2$ together denote an alkylidene or benzylidene protective group,
R$^4$ denotes a hydrogen atom, an acyl or benzyl protective group or a 2,3,4-tri-O-benzyl-α-L-fucopyranosyl or α-L-fucopyranosyl radical,
R$^5$ denotes H, OH, NH$_2$, NHNH$_2$, N$_3$, O-alkyl, O-aryl, NH—(CH$_2$)$_m$NH$_2$, where m=2–5, lysine, polylysine or a carrier,
n denotes a number from 1 to 10 and
R$^3$ denotes a hydrogen atom, an acyl or benzyl protective group or an α-D-glycopyranosyl radical of the general formula II

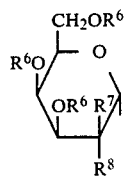

in which
R$^6$ denotes a hydrogen atom or an acyl or benzyl protective group,
R$^7$ denotes a hydrogen atom or halogen and
R$^8$ denotes a hydrogen atom, an acyloxy or benzyloxy group or an azido, amino, acetamido or hydroxyl group,
and to a process for their preparation and their use, when bonded to a carrier, as synthetic antigens, glycolipids or immuno-adsorbents.

The surface of human erythrocytes is, in the same way as other cell types, covered with a mosaic of specific determinants which consists of a large number of complex oligosaccharide chains. It is known (R. R. Race and R. Sänger, Blood Groups in Man, Blackwell Scientific Publ., Oxford 1975) that carbohydrate compounds are the antigen determinants of numerous substances. Oligosaccharides, which themselves have no antigenic action, have antigenic properties if they are bonded to a suitable high-molecular carrier.

To prepare synthetic antigens and immuno-adsorbents with structural features of the determinants active in respect of the ABO blood groups, chemical compounds which have these structural features and can be reacted with suitable carrier molecules are needed.

It is known that carbohydrates become synthetic antigens when they are bonded to a carrier via a spacer.

The object of the present invention was to prepare compounds from which synthetic ABO blood group-active antigens, immuno-adsorbents and glycolipids can be prepared by covalent bonding to a carrier.

This object is achieved by preparing compounds of the general formula I and bonding them to a carrier.

Preferred compounds of the formula I are those in which the carbohydrate radical is β-D-galactopyranosyl, or
R$^1$ and R$^2$ are hydrogen atoms,
R$^4$ is a hydrogen atom or α-L-fucopyranosyl,
R$^3$ is hydrogen, N-acetyl-α-D-galactosaminyl, α-D-galactopyranosyl or 2-deoxy-α-D-galactopyranosyl,
R$^5$ is OCH$_3$, NHNH$_2$, N$_3$, NH—CH$_2$CH$_2$NH$_2$, a protein, in particular albumin, a gel carrying NH$_2$ groups or cephalin and n=7.

The process according to the invention for the preparation of one of the new compounds of the formula I comprises (a) reacting a compound of the general formula III

$$HOCH_2CH_2NHCO(CH_2)_nCOR^5 \quad \text{III}$$

in which R$^5$ denotes O-alkyl or O-benzyl and n is a number from 1 to 10, with a compound of the general formula IV

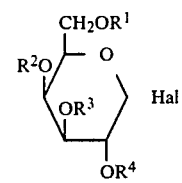

in which R$^1$, R$^2$, R$^3$ and R$^4$ denote acyl groups, preferably acetyl or benzoyl groups, and Hal denotes Cl, Br or I, in a manner which is known per se, preferably to give a β-glycoside of the formula I, (b) splitting off the acyl groups in the product from stage (a) under alkaline conditions in a manner which is known per se and converting the compound into a 4,6-O-alkylidene or 4,6-benzylidene compound of the formula I in which R$^3$ and R$^4$ each denote a hydrogen atom and R$^1$ and R$^2$ together denote the benzylidene or an alkylidene group, (c) converting the product from stage (b) into a compound of the general formula I in which R$^3$ denotes an acyl group, preferably an acetyl or benzoyl group, in a manner which is known per se, (d) reacting the product from stage (c) with a 2,3,4-tri-O-benzyl-α-L-fucopyranosyl halide in a manner which is known per se to give an α-linked disaccharide derivative of the formula I in which
R$^2$ is 2,3,4-tri-O-benzyl-α-L-fucopyranosyl, and if desired de-blocking the product to give a further compound of the formula I, (e) selectively splitting off the 3-O-acyl group in the blocked product from stage (d) in a manner which is known per se, whereupon a compound of the formula I in which R$^4$ is 2,3,4-tri-O-benzyl-α-fucopyranosyl, R$^3$ is hydrogen and R$^1$, R$^2$ and R$^5$ have the meanings given for formula IV is obtained, (f) reacting the product from stage (e) with a compound of the general formula V

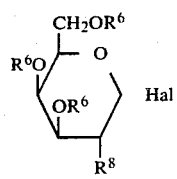

in which
- R⁶ is an acyl group, preferably an acetyl or benzyl group,
- R⁸ is the azido or benzyloxy group and Hal is Br or Cl, in a manner which is known per se to give an α-linked trisaccharide derivative of the formula I in which
- R⁴ is 2,3,4-tri-O-benzyl-α-L-fucopyranosyl and
- R³ is 3,4,6-tri-O-benzyl-2-azido-α-L-galactopyranosyl, and if desired de-blocking the product to give further compounds of the formulae VI and VII

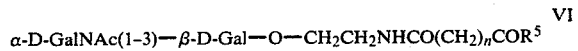

VI

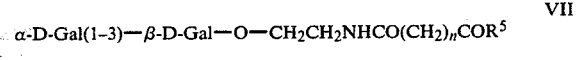

VII

(g) reacting the product from stage (e) with 3,4,6-tri-O-acetyl-D-galactal in the presence of N-iodo- or -bromosuccinimide in a manner which is known per se to give an α-linked trisaccharide derivative of the formula I in which R⁴ is 2,3,4-tri-O-benzyl-α-L-fucopyranosyl and R³ is 3,4,6-tri-O-acetyl-2-bromo- or -iodo- -D-galactosyl, and if desired de-blocking the product to give a further compound of the formula VIII 2-desoxy-                    VIII

and (h) converting a compound, obtained as described above, of the formula I in which R⁵ is O-alkyl or O-aryl into a compound of the formula I in which R⁵ denotes OH, NH—NH₂, N₃, HN—(CH₂)$_m$—NH₂, where m is a number from 2 to 5, lysine, polylysine, an NH-protein, a gel carrying NH₂ groups or NH-cephalin, in a manner which is known per se.

The products from stage (h), in which R⁵ is an azido group, can be bonded to soluble or insoluble carriers carrying amino groups, with the formation of an acid amide grouping, in a manner which is known per se.

Examples of such carriers are peptides and proteins, preferably human or bovine serum albumin, polylysine, aminated plastics or gels, preferably silica gel activated or aminated with ethylenediamine, or aminated poly-saccharides or lipids, preferably cephalins or aminated phospholipids.

The products from stage (h) which contain an NH—(CH₂)$_m$—NH₂ grouping can be bonded via the primary amino group to soluble or insoluble carriers containing an oxirane grouping, with the formation of secondary amines, in a manner which is known per se.

The carrier-bonded compounds of the formula I in which R⁴ is α-L-fucopyranosyl and R³ is hydrogen, N-acetyl-α-D-galactosaminyl,α-D-galactopyranosyl or 2-deoxy-α-D-galactopyranosyl are synthetic antigens or immuno-adsorbents.

The examples which follow illustrate the invention:

EXAMPLE 1

N-(8-Methoxycarbonylcapryl)-2-aminoethyl-2,3,4,6-tetra-O-acetyl-β-D-galactopyranoside (Compound 1)

20 g (81.5 mmoles) of N-(8-methoxycarbonylcapryl)-2-aminoethanol were dissolved in 1,000 ml of benzene/nitromethane 1:1. After 250 ml of the solvent mixture had been distilled off, 20.6 g (81.5 mmoles) of Hg(CN)₂ and 35.2 g (85.6 mmoles) of 2,3,4,6-tetra-O-acetyl-α-D-galactopyranosyl bromide, dissolved in 400 ml of benzene/nitromethane 1:1, were slowly added at 60° C., while stirring and with exclusion of moisture. After the mixture had been stirred for 1.5 hours, a further 1.7 g of 2,3,4,6-tetra-O-acetyl-α-D-galactopyranosyl bromide were added. After 15 minutes, the alcoholic components had reacted completely (thin layer chromatography:chloroform/methanol 9:1). The reaction solution was diluted with 500 ml of chloroform and the filtrate was washed twice with 10% strength aqueous potassium iodide solution and three times with saturated aqueous sodium bicarbonate solution, dried over sodium sulfate and concentrated to give a syrup (50 g). 1 g of the resulting crude compound was purified by chromatography (CHCl₃/acetone 4:1; 25 g of silica gel) for the determination of analytical and spectroscopic data.

Yield: 50 g (crude product) of syrup
$[\alpha]_D^{20} = 2.49°$ (C=1 in CHCl₃)
¹H-NMR (270 MHz, CD₃OD) δ: H-1 4.62 d ppm (J$_{1,2}$=7.9 Hz); H-2 5.10 dd (J$_{2,3}$=10.5 Hz); H-3 3.4 dd; and Ac 2.15 s, 2.04 s, 1.94 s.

calculated: C,54.25H,7.18; N,2.43. found: C, 54.22; H, 7.15; N 2.39.

EXAMPLE 2

N-(8-Methoxycarbonylcapryl)-2-aminomethyl-4,6-O-benzylidene-β-D-galactopyranoside (Compound 2)

50 g of compound 1 were dissolved in 200 ml of dry methanol and the solution was adjusted to pH 11 with 0.1 molar methanolic sodium methylate solution. The solution was left to stand at room temperature for 8 hours, with exclusion of moisture. The reaction mixture was neutralized with the activated ion exchanger Dowex 50 WX and, after the resin had been filtered off, was concentrated to give a syrup. 350 ml of freshly distilled benzaldehyde and 40 g of dry zinc chloride were added to the crude product (42 g), with exclusion of moisture. After the mixture had been stirred at room temperature for 12 hours, the reaction was complete (thin layer chromatography:chloroform/methanol 5:1). The reaction mixture was stirred intensively with aqueous sodium bicarbonate solution for 10 minutes. After the inorganic precipitate had been filtered off, the filtrate was extracted three times with chloroform. The combined inorganic phases were dried over sodium sulfate and the solution was concentrated, first in vacuo and then under a high vacuum, to give a syrup. The product crystallized out in acetonitrile/diisopropyl ether.

Yield: 24 g (60%); $[\alpha]_D^{20} = 12.87°$ C. (c=1; chloroform)

$^1$H-NMR: Compound 2 was characterized as the 2,3-di-O-acetyl derivative (compound 4).

calculated: C, 60.59; 7.53; N, 2.82. found: C, 60.90; H, 7.51; N, 2.80.

EXAMPLE 3

N-(8-Methoxycarbonylcapryl)-2-aminoethyl-3-O-acetyl-4,6-O-benzylidene-β-D-galactopyranoside (compound 3)

10 g (20 mmoles) of compound 2 were dissolved in a mixture of 500 ml of dry methylene chloride and 20 ml of dry pyridine. 1.73 g (22 mmoles) of acetyl chloride, dissolved in 10 ml of dry methylene chloride, were added dropwise at −20° C. After 30 minutes, the starting compound had reacted completely (thin layer chromatography: chloroform/acetone 1:1). After the reaction mixture had been concentrated, the resulting syrup was taken up in chloroform and the mixture was washed twice with dilute HCl and then with water, dried over sodium sulfate and, after filtration, concentrated to give a syrup. The crude product was then purified by chromatography (100 g of silica gel; eluting agent: CHCl$_3$/acetone 1:1).

Yield: 10 g (91%) of syrup $[\alpha]_D^{20} = 40.0°$ (c=1; chloroform)

$^1$H-NMR (400 MHz, CDCl$_3$) δ: H-1 4.33 d ppm ($J_{1,2}$=8 Hz); H-2 3.92 dd ($J_{2,3}$=10.5); H-3 4.77 dd ($J_{3,4}$4.2 Hz); and Ac 2.05 s calculated: C, 60.32; H, 7.31; N, 2.61. found: C, 60.34; , H 7.30; N, 2.58.

EXAMPLE 4

N-(8-Methoxycarbonylcapryl)-2-aminoethyl-2,3-di-O-acetyl-4,6-O-benzylidene-β-D-galactopyranoside (compound 4)

1 g (2 mmoles) of compound 2 were reacted with 0.346 g (4.4 mmoles) of acetyl chloride as described in Example 3, and the mixture was worked up.

Yield: 1.1 g (95%) of syrup $[\alpha]_D^{20} = +32.58°$ (c=1; chloroform)

$^1$H-NMR (100 MHz, CDCl$_3$) δ: H-1 4.52 d ppm ($J_{1,2}$=3.8 Hz); and Ac 2.04 s, 2.05 s calculated: C, 60.09; H 7.13; N, 2.42. found: C, 59.96; H, 7.08; N, 2.29.

EXAMPLE 5

N-(8-Methoxycarbonylcapryl)-2-aminoethyl-3-O-benzoyl-4,6-O-benzylidene-β-D-galactopyranoside (compound 5)

5 g (10 mmoles) of compound 2 were dissolved in a mixture of 10 ml of dry acetonitrile and 20 ml of dry pyridine. 1.32 g (10 mmoles) of benzoyl cyanide, dissolved in 10 ml of dry acetonitrile, were added dropwise at −5° C. in the course of 30 minutes, with exclusion of moisture. After the reaction mixture had been stirred at −5° C. for 4 hours, methanol was added and the mixture was concentrated. The resulting syrup was taken up in chloroform and the mixture was washed twice with dilute HCl and then with water, dried and concentrated. The crude product (7.5 g) was then purified by chromatography (70 g of silica gel, CHCl$_3$/acetone 4:1).

Yield: 5.2 g (86%)

Melting point =95° C. $[\alpha]_D^{20} = +72.1°$ (c=1; chloroform)

$^1$H-NMR (270 MHz, CDCl$_2$) δ: H-1 4.37 d ppm ($J_{1,2}$=7.9 Hz); H-2 4.07 dd ($J_{2,3}$=10.6 Hz); H-3 5.07 dd ($J_{3,4}$=3.6 Hz); and PhCH 5.45 s calculated: C, 64.09; H, 6.89; N, 2.34. found: C, 64.04; H, 7.00; N, 2.23.

EXAMPLE 6

N-(8-Methoxycarbonylcapryl)-2-aminoethyl-2-O-(2,3,4-O-benzyl-L-fucopyranosyl)-4,6ri-O-benzylidene-D-galactopyranoside (compound 6)

10 g (19 mmoles) of compound 3, 4.8 g (19 mmoles) of mercury-II cyanide, 40 g of molecular sieve 4 Å (powder) were first distilled with toluene and then suspended in 400 ml of dry methylene chloride at room temperature, with exclusion of moisture. 11 g (22.8 mmoles) of freshly prepared 2,3,4-tri-O-benzyl-α-L-fucopyranosyl bromide, dissolved in 100 ml of dry methylene chloride, were added dropwise to the suspension in the course of 3 hours. After the mixture had been stirred for 1 hour, a further 2.2 g (4.5 mmoles) of 2,3,4-tri-O-benzyl-α-L-fucopyranosyl bromide were added dropwise. The reaction to give the disaccharide had ended completely after a further 6 hours (thin layer chromatography: chloroform/acetone 4:1). The suspension was filtered over Celite and the residue was carefully washed with methylene chloride. The combined filtrates were washed twice with aqueous KI solution, twice with aqueous sodium bicarbonate solution and once with water. After the mixture had been concentrated, the resulting syrup was then distilled with toluene.

A small amount of the crude product was purified by column chromatography for analytical and spectroscopic purposes.

For deacetylation, the crude product (26 g) was dissolved in methanol, and methanolic sodium methylate solution was added. After customary working up, the product was purified by column chromatography (CHCl$_3$/acetone 4:1; 150 g of silica gel).

Yield: 14.5 g (81%), amorphous

Melting point=126° C.

$[\alpha]_D^{20}=49.6°$ (C=1.5 in CHCl$_3$)

$^1$H-NMR (400 MHz, CDCl$_3$) δ: H-1 4.34 ppm ($J_{1,2}$=7.7 Hz); H-2 3.83 dd ($J_{2,3}$=9.5); H-3 3.78 dd; H-1' 5.09 d ($J_{1',2'}$=3.4 Hz) H-2' 4.07 dd ($J_{1',2'}$=10.2 Hz); H-6' 1.13 d ($J_{5',6'}$=6 Hz); and PhCH 5.58 s.

calculated: C, 68.48; H,7.18; N, 1.54. found: C, 68.80; H, 7.20; N, 1.5.

EXAMPLE 7

N-(8-Methoxycarbonylcapryl)-2-aminoethyl-3-O-benzoyl-2-O-(2,3,4-tri-O-benzyl-α-L-fucopyranosyl)-4,6-O-benzylidene-β-D-galactopyranoside (compound 7).

10 g (17 mmoles) of compound 5 were converted into a disaccharide in the same manner as described in

EXAMPLE 6

Yield: 13.5 g (81%)

$[\alpha]_D^{20} = -34.9°$ (C=1 in CHCl$_3$)

$^1$H-NMR (270 MHz, CDCl$_3$) δ: H-1 4.36 d ppm; H-3 5.34 ($J_{2,3}$=9.8 Hz; $J_{3,4}$=3.6 Hz); H-1' 5.24 ($J_{1',2'}$=3.3 Hz).

calculated: C, 69.74; H, 6.84; N, 1.38. found: C, 69.62; H,6.82; N,1.31.

Compound 7 was deacetylated to compound 6 in the same manner as described in Example 6.

EXAMPLE 8

N-(8-Methoxycarbonylcapryl)-2-aminoethyl-2-O-(2,3,4-tri-O-benzyl-α-L-fucopyranosyl)-3-O-(2,3,4,6-tetra-O-benzyl-α-D-galactopyranosyl)-4,6-O-benzylidene-β-D-galactopyranoside (compound 8).

5 g (5.58 mmoles) of compound 6, 14.1 g (55.8 mmoles) of mercury cyanide, 2.0 g (5.58 mmoles) of mercury bromide, 50 g of molecular sieve 4 Å and 10 g of Drierite were distilled with toluene and then suspended in 350 ml of dry methylene chloride. The suspension was stirred for 1 hour, with exclusion of moisture. After 9.6 g (16.74 mmoles) of 2,3,4,6-tetra-O-benzyl-α-D-galactopyranosyl bromide, dissolved in 100 ml of dry methylene chloride, had been added, the suspension was stirred for 24 hours under a N$_2$ atmosphere and whilst simultaneously removing HCN. The mixture was filtered with CH$_2$Cl$_2$ and rinsed. The organic phase was washed twice with aqueous KI solution, then with aqueous sodium bicarbonate solution and subsequently with water and concentrated. The syrup was purified by chromatography (400 g of silica gel; chloroform/acetone 20:1 and chloroform/acetone/methanol 4:1:1).

Yield: 6.7 g (86%) of syrup $[\alpha]_D^{20} = -13.4°$ (C=1 in CHCl$_3$)

$^1$H-NMR (270 MHz, CDCl$_3$) δ: H-1 4.64 d ppm (J$_{1,2}$=7.4 Hz); H-1' 5.32 d (J$_{1',2'}$=3.1 Hz); H-1" 5.33 d (J$_{1",2"}$=2.9 Hz) and PhCH 5.53 s.

calculated: C, 72.00; H, 6.95; N, 0.98. found: C, 71.73; H, 6.96; N, 0.93.

EXAMPLE 9

N-(8-Methoxycarbonylcapryl)-2-aminoethyl-2-O-(α-L-fucopyranosyl)-3--O-(α-d-galactopyranosyl)-β-D-galactopyranoside (compound 9).

6 g (4.4 mmoles) of compound 8 were dissolved in 400 ml of freshly distilled glacial acetic acid and hydrogenated in the presence of 6 g of palladium-on-charcoal (10%) for 20 hours at room temperature. The mixture was then filtered, the residue was rinsed with glacial acetic acid and the filtrate was concentrated in vacuo. The residue was dissolved in methanol and the solution was filtered over Celite. The product crystallized from ethanol/ethyl acetate.

Yield: 2.7 g (81%) amorphous $[\alpha]_D^{20} = -22.98°$ (c=1 H$_2$O)

Melting point=170° C.

$^1$H-NMR (400 MHz, CDCl$_3$) δ: H-1 4.57 d ppm (J$_{1,2}$=7.8 Hz); H-1' 5.28 d (J$_{1',2'}$=3.3 Hz); H-1" 5.27 d (J$_{1",2"}$=3.2 Hz).

calculated: C, 50.34; H, 7.46; N, 1.96. found: C, 49.90; H, 7.31; N 1.91.

Example 10

N-(8-Methoxycarbonylcapryl)-2-aminoethyl-3-O-(2-azido-2-deoxy-α-D-galactopyrancsyl)-2-O-(2,3,4-tri-O-benzyl-α-D-fucopyranosyl)-4,6-O-benzylidene-β-D-galactopyranoside (compound 10).

7.47 g (8.3 mmoles) of compound 6, 6.32 g (24.9 mmoles) of mercury cyanide, 9.01 g (24.9 mmoles) of mercury bromide and 50 g of molecular sieve 4 Å were first distilled with toluene and then suspended in 40 ml of dry methylene chloride. The suspension was stirred for 1 hour with exclusion of moisture. After 10 g (24.9 mmoles) of 3,4,6-tri-O-acetyl-2-azido-2-deoxy-D-pyranosyl bromide, dissolved in 150 ml of dry methylene chloride, had been added, the suspension was stirred for 48 hours under a N$_2$ atmosphere and while simultaneously removing the HCN liberated. 250 ml of methylene chloride were added to the reaction mixture, the mixture was filtered and the filtrate was washed twice with aqueous KI solution, twice with saturated sodium bicarbonate solution and once with water. The organic phase was dried with sodium sulfate and concentrated in vacuo and the residue was distilled with toluene. The resulting syrup (13.3 g) was dissolved in dry methanol and the solution was adjusted to pH 11 with one molar methanolic sodium methylate solution. After 8 hours, the deacetylation had ended. The solution was neutralized with glacial acetic acid and concentrated in vacuo. The resulting syrup was taken up in chloroform and the mixture was washed once with water. After concentration, the product was purified by column chromatography (400 g of silica gel; toluene/acetone 1:1).

Yield: 6.93 g (76%)

IR cm$^{-1}$ (2110, 1740, 1705, 1600, 1500)

calculated: C, 63.37; H, 6.79; N, 5.10. found: C 63.29, H, 6.80; N 5.2.

0.5 g of the product was acetylated, and was characterized by NMR spectroscopy as the 3,4,6-tri-O-acetyl derivative.

$[\alpha]_D^{20} = +28.7°$ (c=1 in CHCl$_3$)

$^1$H-NMR (400 MHz, CDCl$_3$) δ: H-1 4.36 d ppm (J$_{1,2}$=7.6 Hz); H-2 3.95 dd (J$_{2,3}$=10.5 Hz); H-1' 5.12 d (J$_{1',2'}$=3.7 Hz); H-2' 4.03 dd (J$_{2',3'}$=11.0 Hz); H-1" 5.33 d (J$_{1",2"}$=3.5 Hz); H-2"2.55 dd (J$_{2",3"}$=10.3 Hz).

EXAMPLE 11

N-(8-Methoxycarbonylcapryl)-2-aminoethyl-3-O-(2-acetamido-2-deoxy-α-D-galactopyranosyl)-2-O-(α-L-fucopyranosyl)-β-D-galactopyranoside (compound 11)

7.0 g (5.6 mmoles) of compound 10 were dissolved in 300 ml of glacial acetic acid and hydrogenated in the presence of 12 g of palladium-on-charcoal (10%) at room temperature for 96hours. For working up, the mixture was diluted with 100 ml of glacial acetic acid and filtered, the residue was rinsed and the filtrste was evaporated in vacuo. The residue was dissolved in 100 ml of methanol/acetic anhydride 10:1 and the solution was slowly concentrated in vacuo. The amorphous product was dissolved in 150 ml of methanol, and 40 ml of concentrated ammonia were added to the solution. After 24 hours, the thin layer chromatogram showed a uniform substance (CHCl$_3$/CH$_3$OH/H$_2$O 65:35:8). After the mixture had been evaporated in vacuo, the residue was purified over Sephadex G-25.

Yield: 3.15 (76%) amorphous

Melting point=190° C.

$[\alpha]_D^{20} = +31.0°$ (C=1 in H$_2$O)

IR cm$^{-1}$ (1740, 1670)

$^1$H-NMR (400 MHz, D$_2$O) δ: H-1 4.57 d ppm (J$_{1,2}$=7.6 Hz); H-1' 5.28 d (J$_{1',2'}$=3.0 Hz); H-1" 5.18 d (J$_{1",2"}$=3.3 Hz); and Ac 2.05 s calculated: C, 50.79; H, 7.46; N, 3.70. found: C, 50.82; H, 7.50; N, 3.61.

EXAMPLE 12

N-(8-Methoxycarbonylcapryl)-2-aminomethyl-3-O-(3,4,6-tri-O-acetyl-2-deoxy-2-iodo-α-O-talopyranosyl)-3-O-(2,3,4-tri-O-benzyl-β-D-fucopyranosyl)-4,6-O-benzylidene-β-D-galactopyranoside (compound 12)

1 g (1.12 mmoles) of compound 6 and 0.302 g (1.34 mmoles) of N-iodo-succinimide were first distilled with toluene and then dissolved in 30 ml of dry acetonitrile. 0.34 g (1.23 mmoles) of 3,4,6-tri-O-acetyl-D-galactal, dissolved in 30 ml of dry acetonitrile, were added, with exclusion of moisture. The mixture was stirred at 60° C. for 8 hours and then at room temperature for a further 50 hours (thin layer chromatography: toluene/acetone 1:1). Methylene chloride was added to the solution and the mixture was washed with water. The organic phase was concentrated in vacuo and the resulting syrup was purified by chromatography (30 g of silica gel, toluene-/acetone 2:1).

Yield: 1.0 g (73%) of syrup $[\alpha]_D^{20} = +53°$ (C=1 in CHCl$_3$) $^1$H-NMR (400 MHz), CDCl$_3$) δ: H-1 4.41 d ppm ($J_{1,2}$=7.7 Hz); H-1' 5.29 d ($J_{1'2'}$=0.9 Hz); H-1'' 5.35 d ($J_{1'',2''}$=3.4 Hz)

calculated: C, 59.39; H, 6.18; I, 9.82; N, 1.08. found: C, 59.03; H, 6.20; I, 9.37; N, 1.02.

EXAMPLE 13

N-(8-Methoxycarbonyl)-2-aminomethyl-3-O-(2-deoxy-α-D-galactopyranosyl)-2-O-(α-L-fucopyranosyl)-D-galactopyranoside (compound 13)

1 g (0.77 mmole) of compound 12 was dissolved in 80 ml of glacial acetic acid and hydrogenated in the presence of 1.6 g of palladium-on-charcoal (10%) at room temperature for 72 hours. For working up, the mixture was diluted with 50 ml of glacial acetic acid and filtered, the residue was rinsed and the filtrate was concentrated in vacuo. The residue was distilled with toluene and the syrup was then dissolved in a mixture of 20 ml of methanol and 6 ml of concentrated ammonia. After 24 hours, the thin layer chromatogram showed a uniform substarce (CHCl$_3$/methanol/water 65:35:5). After the mixture had been evaporated in vacuo, the residue wes crystallized in methanol/acetone.

Yield: 0.38 g (73%)

$[\alpha]_D^{20} = +53.8°$ (C=1 in H$_2$O)

$^1$H-NMR (400 MHz, D$_2$O) δ: H-1 4.46 d ppm ($J_{1,2}$=7.7 Hz); H-1' 4.67 dd ($J_{1'2'e}$ =1.0 Hz, $J_{1'2'e}$ =3.6 Hz); H-1'' 5.21 d ($J_{1'',2''}$=3.2 Hz) IR cm$^{-1}$ (1740, 1660)

calculated: C, 52.70; H, 7.75; N, 2.05. found: C, 52.81; H, 7.73; N, 2.01.

EXAMPLE 14

Inhibition of human anti-A with compound 11 and human anti-B with compound 9

Hemaglutination of a 5% strength A-erythrocyte suspension with human anti-A (titer 2$^{-5}$) was inhibited completely by compound 11 (0.5 mg/ml). Compound 9 exhibited no inhibition.

Hemaglutination of a 5% strength B-erythrocyte suspension with human anti-B (titer 2$^{-5}$) was inhibited completely by compound 9 (0.3 mg/ml). Compound 11 exhibited no inhibition.

EXAMPLE 15

N-[8-(2-Aminoethylcarbamoyl)-capryl]-2-aminoethyl-3-O-(2-acetamido-2-deoxy-α-D-galactopyranosyl)-2-O-(α-D-fucopyranosyl)-β-D-galactopyranoside (compound 15)

100 mg (0.13 mmole) of compound 11 were dissolved in 20 ml of 85% strength aqueous 1,2-diaminoethane and the solution was stirred at room temperature for 24 hours (thin layer chromatography: CHCl$_3$/methanol/-concentrated NH$_3$2:2:1). The mixture was freeze-dried and the amorphous residue was then distilled several times with methanol/toluene. Compound 15 was detected by thin layer chromatography (CHCl$_3$/methanol/concentrated NH$_3$ 1:2:1, spray reagent: ninhydrin).

Yield: 100 mg

IR (2 mg/100 mg of KBr) cm$^{-1}$ (3500–3200, 1640)

As described in Example 15, the following compounds were prepared and were characterized by thin layer chromatography and IR spectroscopy.

N-(8-(2-Aminoethylcarbamoyl)-capryl)-2-aminoethyl-β-D-galactopyranoside (compound 16)

N-(8-(2-Aminoethylcarbamoyl)-capryl)-2-aminoethyl-2-O-(α-L-fucopyranosyl)-β-D-galactopyranoside (compound 17)

N-(8-(2-Aminoethylcarbamoyl)-capryl)-2-aminoethyl-3-O-(α-D-galactopyranosyl)-2-O-(α-D-fucopyranosyl)-β-D-galactopyranoside (compound 18)

N-(8-(2-Aminoethylcarbamoyl)-capryl)-2-aminoethyl-3-O-(2-deoxy-α-D-galactopyranosyl)-2-O-(α-L-fucopyranosyl)-β-D-galactopyranoside (compound 19)

EXAMPLE 16

N-(8-Hydrazinocarbonylcapryl)-2-aminoethyl-3-O-(α-D-galactopyranosyl)-2-O-(α-D-fucopyranosyl)-β-D-galactopyranoside (compound 20)

100 mg (140 μmoles) of compound 9 were stirred in 5 ml of 80% strength aqueous hydrazine hydrate at room temperature for 24 hours (thin layer chromatography: ethyl acetate/methanol/water 5:3:3). The solution was freeze-dried and the amorphous residue was then distilled several times with methanol/toluene.

Yield: 100 mg

IR (2 mg of sample/100 mg of KBr) cm$^{-1}$ (3500–3200, 1680, 1640).

As described in Example 16, the following compounds were prepared and were characterized by thin layer chromatography and IR spectroscopy:

N-(8-Hydrazinocarbonylcapryl)-2-aminoethyl-β-D-galactopyranoside (compound 21)

N-(8-Hydrazinocarbonylcapryl)-2-aminoethyl-2-O-(α-L-fucopyranosyl)-β-D-galactopyranoside (compound 22)

N-(8-Hydrazinocarbonylcapryl)-2-aminoethyl-3-O-(2-acetamido-2-deoxy-α-D-galactopyranocyl)-2-O-(α-L-fucopyranosyl)-β-D-galactopyranoside (compound 23)

N-(8-Hydrazinocarbonylcapryl)-2-aminoethyl-3-O-(2-deoxy-α-D-galactopyranosyl)-2-O α-L-fucopyranosyl)-β-D-galactopyranoside (compound 24)

EXAMPLE 17

N-(8-Azidocarbonylcapryl)-2-aminoethyl-3-O-(α-D-galactopyranosyl)-2-O-(α-L-fucopyranosyl)-β-D-galactopyranoside (compound 25)

200 mg (280 μmoles) of compound 20 were dissolved in 2 ml of dry dimethylformamide and the solution was cooled to −25° C. A solution of 0.3 ml of dry dioxane containing 3.5 N hydrochloric acid was added, and 45.2 mg (380 μmoles) of iso-pentyl nitrite, dissolved in 1 ml of dry dimethylformamide, were then added. This mixture was stirred at −25° C. for 30 minutes, and 28 mg (300 μmoles) of amidosulfuric acid were then added (thin layer chromatography: ethyl acetate/methanol/water 5:3:3).

The reaction was monitored by thin layer chromatography (Rf=0.45). The solution containing the carboxylic acid azide (compound 25) was used for the reaction with aminated carriers without further purification steps.

As described in Example 17, the following compounds were prepared and were characterized by thin layer chromatography:

N-(8-Azidocarbonylcapryl)-2-aminoethyl-β-D-galactopyranoside (compound 26)

N-(8-Azidocarbonylcapryl)-2-aminoethyl-2-O-(α-L-fucopyranosyl)-β-D-galactopyranoside (compound 27)

N-(8-Azidocarbonylcapryl)-2-aminoethyl-3-O-(2-acetamido-2-deoxy-α-D-galactopyranosyl)-2-O-(α-L-fucopyranosyl)-β-D-galactopyranoside (compound 28)

N-(8-Azidocarboxylcapryl)-2-aminoethyl-3-O-(2-deoxy-α-D-galactopyranosyl)-2-O-(α-L-fucopyranosyl)-β-D-galactopyranoside (compound 29)

EXAMPLE 18

N-(8-Hydroxycarbonylcapryl)-2-aminoethyl-2-O-(α-L-fucopyranosyl)-3-O-(α-D-galactopyranosyl)-β-D-galactopyranoside (compound 30)

100 mg (140 μmoles) of compound 9 were treated with 4 ml of 0.1 N aqueous NaOH at room temperature (thin layer chromatography: ethyl acetato/methanol/water 5:3:3). After deionization with an ion exchanger, the sample was lyophilized. Yield: 100 mg.

As described in Example 18, the following compounds were prepared and were characterized by thin layer chromatography:

N-(8-Hydroxycarbonylcapryl)-2-aminoethyl-2-O-β-D-galactopyranoside (compound 31)

N-(8-Hydroxycarbonylcapryl)-2-aminoethyl-2-O-(α-L-fucopyranosyl)-β-D-galactopyranoside (compound 32)

N-(8-Hydroxycarbonylcapryl)-2-aminoethyl-3-O-(2-acetamido-2-deoxy-α-D-galactopyranosyl)-2-O-(α-L-fucopyranosyl)-β-D-galactopyranoside (compound 33)

N-(8-Hydroxycarbonylcapryl)-2-aminoethyl-3-O-(2-deoxy-α-D-galactopyranosyl)-2-O-(α-L-fucopyranosyl)-β-D-galactopyranoside (compound 34)

Compounds 30 to 34 were coupled to proteins (human serum albumin) or polypeptides (polylysine) by known processes either directly with a carbodiimide (for example 1-ethyl-3-(3′-dimethylaminopropyl)-carbodiimide hydrochloride or as activated esters (for example N-hydroxysuccinimide derivatives).

EXAMPLE 19

Immobilization of aminated haptenes (compounds 15 to 19) on the carrier Eupergit C carrying oxirane groups or with epichlorohydrin-activated Magnogel.

5 g of Eupergit C (Messrs. Röhm Pharma) were suspended in phosphate buffer of pH 7.2 (50 ml) and the suspension was left to stand at room temperature for 16 hours. The carrier was washed with $CO_2$-free water and then with 1/15 molar aqueous $Na_2HPO_4$ and $Na_2B_4O_7$ solution (pH 9.2) and the volume was adjusted to 50 ml. 50 μmoles of an aminated compound were added to this suspension and the mixture was shaken at room temperature for 24 hours. A further 5 ml of 10% strength aqueous ethanolamine solution was added to react the remaining oxirane groups of the carrier, and the suspension was shaken again for 48 hours.

The immuno-adsorbent was washed with water and then with phosphate buffer. The moist gel was stored at 4° C.

Analytical determination of the D-galactose or L-fucose in the immuno-adsorbent:

| Immobilized compound | μmoles of sugar/g of carrier | | | |
|---|---|---|---|---|
| | Gal | | Fuc | |
| | calculated | found | calculated | found |
| 15 | 10 | 10 | 10 | 9.3 |
| 16 | 10 | 9.6 | — | — |
| 17 | 10 | 9.8 | 10 | 10 |
| 18 | 20 | 19.4 | 10 | 10 |
| 19 | 10 | 9.6 | 10 | 9.8 |

EXAMPLE 20

Immobilization of Carbonylazide Derivatives of Haptenes (compounds 25 to 29) on aminated carriers 5 g of aminated Eupergit C (for the preparation process, see below) were suspended in 18 ml of 0.08 M $Na_2B_4O_7$ buffer and 0.35 M $KHCO_3$ buffer. The carbonylazide derivative (compounds 25 to 29), prepared in situ, was added dropwise to the suspension at 0° C. and the mixture was then shaken for a further 24 hours at 4° C. The immuno-adsorbent was washed with $CO_2$-free water and then taken up in 18 ml of aqueous saturated $NaHCO_3$ solution, and 18 ml of 5% strength acetic anhydride were added. After the mixture had been shaken for 15 minutes, the adsorbent was filtered off and washed with water, then with 2% strength aqueous ammonia solution and finally with water. The moist immuno-adsorbent was stored at 4° C.

Amination of Oxirane-Activated Carriers 50 g of oxirane-activated carrier (preferably Eupergit C or Magnogel activated with epichlorohydrin) were suspended in 500 ml of distilled $CO_2$-free water for 2 hours. After 27.5 ml (0.63 mole) of 1,2-diaminoethane had been added, the suspension was stirred at room temperature for 1 hour. After filtration and washing with distilled water and ethanol, the carrier was dried at 40° C. for 1 hour. By this process, 1 g of carrier contains at least 1.2 mmoles of primary amino groups.

| Analytical determination of the D-galactose or L-fucose in the immuno-adsorbent | | | | |
|---|---|---|---|---|
| | μmoles of sugar/g of carrier | | | |
| | Gal | | Fuc | |
| Immobilized compound | calculated | found | calculated | found |
| 25 | 20 | 20 | 10 | 10 |
| 26 | 10 | 9.8 | — | — |
| 27 | 10 | 9.9 | 10 | 9.6 |
| 28 | 10 | 9.4 | 10 | 9.6 |
| 29 | 10 | 9.7 | 10 | 9.7 |

EXAMPLE 21

Immuno-Adsorption Of Anti-A Serum On A Blood Group A-Active Immuno-Adsorbent 5 g of immuno-adsorbent A (Example 20, compound 28) were suspended in 100 ml of 0.9% strength NaCl solution and the suspension was introduced into a small chromatography column and washed with 150 ml of 0.9% strength NaCl solution. 100 ml of serum (with anti-A titer 1:64) were chromatographed. The immuno-adsorbent was washed with NaCl solution and the adsorbed anti-A antibody was then desorbed with 20 ml of eluting agent (1% strength aqueous ammonia, 0.1 mole of N-acetylaminoethanol and 0.9 mole of ethylene glycol). After the eluting agent had been washed out, the carrier was washed with 150 ml of NaCl solution and can thus be used again for the next chromatographic separation.

The sera were chromatographed with anti-B on immuno-adsorbent B (Example 20, compound 25) in the same manner.

The chromatographed sera showed no anti-A or anti-B titer on serological investigation.

When immuno-adsorbent A or B was used in a "batch process", it was possible to reduce substantially the antibody titer (anti-A or anti-B).

I claim:
1. A compound of the formula I

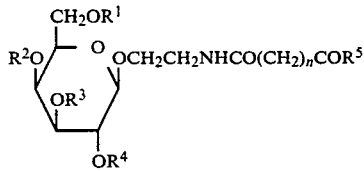

in which
$R^1$ and $R^2$ each denote a hydrogen atom or an acetyl or benzoyl or benzyl group,
Rhu 1 and $R^2$ together denote an alkylidene or benzylidene protective group,
$R^4$ denotes a hydrogen atom, an acetyl or benzoyl or benzyl group or a 2,3,4-tri-O-benzyl-α-L-fucopyranosyl or α-L-fucopyranosyl radical,
$R^5$ denotes H, OH, $NH_2$, $NHNH_2$, $N_3$, -O-alkyl, -O-aryl, $NH-(CH_2)_mNH_2$, where m=2-5, lysine, polylysine or a carrier,
n denotes a number from 1 to 10 and $R^3$ denotes a hydrogen atom, an acetyl or benzoyl or benzyl group or an α-D-glycopyranosyl radical of the general formula II, $$\begin{array}{c} CH_2OR^6 \\ R^6O \overset{}{\underset{OR^6\ R^7}{\diagup\!\!\!\diagdown}} O \\ R^8 \end{array}$$

in which
$R^6$ denotes a hydrogen atom or an acetyl or benzoyl or benzyl group,
$R^7$ denotes a hydrogen atom or halogen and
$R^8$ denotes a hydrogen atom, an acetyloxy or benzoyloxy or benzyloxy group or an azido, amino, acetamido or hydroxyl group.

2. A compound of the formula I $$\begin{array}{c} CH_2OR^1 \\ R^2O \overset{}{\underset{OR^4}{\diagup\!\!\!\diagdown}} O \\ OR^4 \end{array} OCH_2CH_2NHCO(CH_2)_nCOR^5$$

in which the carbohydrate radical is β-D-galactopyranosyl, or $R^1$ and $R^2$ are hydrogen atoms, $R^4$ is α-L-fucopyranosyl, $R^3$ is hydrogen, N-acetyl-α-D-galactosaminyl, α-D-galactopyranosyl or 2-deoxy-α-D-galactopyranosyl, $R^5$ is $OCH_3$, $NHNH_2$, $N_3$, $NH-CH_2CH_2$, human serum albumin, a gel carrying $NH_2$ groups or cephalin and n=7.

3. An antigen composition comprising an effective amount of a compound as claimed in claim 1 bonded to a pharmaceutically acceptable carrier.

4. A method for detecting immunologically active molecules comprising:
(a) contacting the composition of claim 3 with a solution containing said immonologically active molecule, and
(b) detecting the interaction of asid composition with said immunologically active molecule.

5. A method for detecting antibodies comprising:
(a) contacting the composition of claim 3 with a solution containing said antibodies, and
(b) detecting the interaction of said composition with said antibody.

6. A method of chromatographic separation of an antibody from a solution of suspension containing said antibody comprising:
(a) contacting said solution of suspension with a composition comprising a compound of claim 1 bonded to a carrier, which composiition is an active immuno-adsorbent of said antibody,
(b) immuno-adsorbing said antibody on said composition, and
(c) eluting said antibody from said composition.

* * * * *